US 6,726,630 B2

(12) United States Patent
Kawagishi

(10) Patent No.: US 6,726,630 B2
(45) Date of Patent: Apr. 27, 2004

(54) ULTRASOUND DIAGNOSIS APPARATUS FOR IMAGING WITH A CONTRAST AGENT

(75) Inventor: Tetsuya Kawagishi, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/290,147

(22) Filed: Nov. 8, 2002

(65) Prior Publication Data
US 2003/0092992 A1 May 15, 2003

(30) Foreign Application Priority Data

Nov. 8, 2001 (JP) ........................................ 2001-343577

(51) Int. Cl.[7] ................................................. A61B 8/14
(52) U.S. Cl. ..................................................... 600/458
(58) Field of Search ............................... 600/407–471; 73/620–633; 367/2, 11, 130, 138; 128/916

(56) References Cited

U.S. PATENT DOCUMENTS 5,980,459 A * 11/1999 Chiao et al. ................ 600/447
6,074,348 A * 6/2000 Chiao et al. ................ 600/443
6,132,377 A * 10/2000 Bolorforosh et al. ....... 600/458
6,213,951 B1 4/2001 Krishnan et al.

* cited by examiner

Primary Examiner—Ali M. Imam
(74) Attorney, Agent, or Firm—Oblon, Spivak, McClelland, Maier & Neustadt, P.C.

(57) ABSTRACT

Ultrasound diagnosis apparatus includes a transceiver unit, an adding processor, a filter, and an image processor. The transceiver unit insonifies an object injected with a contrast agent via an ultrasound transmission signal transmitted at a fundamental frequency f0 with at least two transmission rates. The adding processor adds a first component of the ultrasound echo signal and second component of the ultrasound echo signal. The first component is transmitted at a first rate of the at least two transmission rates and the second component is transmitted at a second rate of the at least two transmission rates. The filter suppresses at least a first frequency band of an addition result that is centered about a frequency 2·f0. The image processor then generates image data based on a suppressing result.

20 Claims, 10 Drawing Sheets

ULTRASOUND DIAGNOSIS APPARATUS FOR IMAGING WITH A CONTRAST AGENT

CROSS-REFERENCE TO RELATED APPLICATION

This application is based upon and claims the benefit of priority from prior Japanese Patent Application No. P2001-343577, filed on Nov. 8, 2001, the entire content of which is expressly incorporated herein by reference.

FIELD

The present invention relates to ultrasound imaging and more particularly to a method and apparatus for obtaining a contrast enhanced image through ultrasound diagnostic imaging with a contrast agent.

BACKGROUND

Generally, contrast agents comprised of numerous microbubbles, and used for an ultrasound diagnosis, are destroyed by insonifying ultrasound waves. Moreover, the higher the insonifying pressure of the insonifying ultrasound waves, the more easily the contrast agents may be destroyed. When exposed to contrast agents, insonifying ultrasound waves exemplify a nonlinear behavior such that a second harmonic component is generated. The second harmonic component enables a realization of an echo component originating from the contrast agents (hereinafter referred to as a contrast echo component). This technique is generally known as a second harmonic imaging technique.

FIG. 1 is an example of a spectral graph showing components of received signals, which are received from an object as a result of applying insonifying ultrasound waves to the consistent with conventional systems and methods. The received signals include the contrast echo component, a fundamental echo component, and a tissue harmonic imaging echo component (hereinafter referred to as a THI echo component). Typically, a specimen examination involving contrast agents emphasizes a second harmonic imaging technique of the contrast echo component, which usually requires an extraction of a frequency band centered about a frequency twice as high as a fundamental frequency f0.

In addition to the contrast echo component, however, the frequency band may also include high concentrations of the THI echo component generated by nonlinear propagation from tissues, and a leakage component of the fundamental echo component leaked to a second harmonic frequency band. The contrast echo component, therefore, is buried in the frequency band by the THI echo component and the fundamental echo component. As a result, visibility of the contrast echo component deteriorates, and it may be difficult to effectively enhance the contrast echo component in an image.

BRIEF SUMMARY

In accordance with an aspect of the invention there is provided an ultrasound diagnosis apparatus for imaging with a contrast agent. The ultrasound diagnosis apparatus comprising a transceiver unit for insonifying an object injected with a contrast agent via an ultrasound transmission signal transmitted at a fundamental frequency f0 with at least two transmission rates and receiving an ultrasound echo signal from the object based on the ultrasound transmission signal, wherein polarities of the ultrasound transmission signal are alternately inversed; an adding processor for adding a first component and a second component of the ultrasound echo signal, wherein the first component is received by the transceiver unit at a first rate of the at least two transmission rates and the second component is received by the transceiver unit at a second rate of the at least two transmission rates; a filter for suppressing at least a first frequency band of an addition result that is centered about a frequency 2·f0; and an image processor for generating first image data based on a suppressing result.

Another aspect of the present invention provides a method of imaging with a contrast agent in an ultrasound diagnosis apparatus. The method comprises insonifying an object injected with a contrast agent via an ultrasound transmission signal transmitted at a fundamental frequency f0 with at least two transmission rates, wherein polarities of the ultrasound transmission signal are alternately inversed; receiving an ultrasound echo signal from the object based on the ultrasound transmission signal; adding a first component and a second component of the received ultrasound echo signal, wherein the first component is received at a first rate of the at least two transmission rates and the second component is received at a second rate of the at least two transmission rates; suppressing at least a first frequency band of an addition result that is centered about a frequency 2·f0; and generating image data based on a suppressing result.

Still another aspect of the present invention provides an ultrasound diagnosis apparatus for imaging with a contrast agent. The ultrasound diagnosis apparatus comprising a transceiver unit for insonifying an object injected with a contrast agent via an ultrasound transmission signal transmitted at a fundamental frequency f0 with at least two transmission rates and receiving from the object an ultrasound echo signal based on the ultrasound transmission signal, wherein the ultrasound transmission signal has a similar wave profile among the at least two transmission rates; a subtracting processor for subtracting a first component of the ultrasound echo signal from a second component of the ultrasound echo signal, wherein the first component is received at a first rate of the at least two transmission rates and the second component is received at a second rate of the at least two transmission rates; a filter for suppressing a frequency band of a subtraction result that is centered about a frequency n·f0, wherein n is a positive integer; and an image processor for generating image data based on a suppressing result.

Another aspect of the present invention provides a method of imaging with a contrast agent in an ultrasound diagnosis apparatus. The imaging method comprises insonifying an object injected with a contrast agent via an ultrasound transmission signal transmitted at a fundamental frequency f0 with at least two transmission rates, wherein the ultrasound transmission signal has a similar wave profile among the at least two transmission rates; receiving from the object an ultrasound echo signal based on the ultrasound transmission signal; subtracting a first component of the ultrasound echo signal from a second component of the ultrasound echo signal, wherein the first component is received at a first rate of the at least two transmission rates and the second component is received at a second rate of the at least two transmission rates; suppressing a frequency band of a subtraction result that is centered about a frequency n·f0, wherein n is a positive integer; and generating image data based on a suppressing result.

In addition, another aspect of the present invention provides an ultrasound diagnosis apparatus for imaging with a contrast agent. The ultrasound diagnosis apparatus comprising a transceiver unit for insonifying an object injected with a contrast agent via an ultrasound transmission signal transmitted at a fundamental frequency f0, and receiving an ultrasound echo signal from the object based on the ultrasound transmission signal; a moving target indication processor for extracting a component of the ultrasound echo signal based on the transmission signal received by the transceiver unit from a moving target of the object; a filter for suppressing a frequency band of the ultrasound echo signal obtained from the moving target indication processor and centered about a frequency n·f0, wherein n is a positive integer; and an image processor for generating image data based on a suppressing result.

Still another aspect of the present invention provides a method of imaging with a contrast agent in an ultrasound diagnosis apparatus. The imaging method comprises insonifying an object injected with a contrast agent via an ultrasound transmission signal transmitted at a fundamental frequency f0; receiving from the object an ultrasound echo signal based on the ultrasound transmission signal; extracting a component of the received ultrasound echo signal from a moving target of the object; suppressing a frequency band of an extracting result that is centered about a frequency n·f0, wherein n is a positive integer; and generating image data based on a suppressing result.

Another aspect of the present invention provides an ultrasound diagnosis apparatus for imaging with a contrast agent. The ultrasound diagnosis apparatus comprising a transceiver unit for insonifying an object injected with a contrast agent via an ultrasound transmission signal transmitted at a fundamental frequency f0, and receiving from the object an ultrasound echo signal based on the ultrasound transmission signal; a reduction processor for reducing at least a fundamental echo component of the ultrasound echo signal; a filter for suppressing a frequency band of a reduction result that is centered about a frequency n·f0, wherein n is a positive integer; and an image processor for generating image data based on a suppressing result.

BRIEF DESCRIPTION OF THE DRAWINGS

The accompanying drawings which are incorporated in and constitute a part of this specification, illustrate several embodiments of the invention and, together with the description, serve to explain the principles of the invention.

DETAILED DESCRIPTION

Reference will now be made in detail to exemplary embodiments of the invention, examples of which are illustrated in the accompanying drawings. Whenever possible, the same reference number will be used throughout the drawings to refer to the same or like parts.

A 'polarity' of signals may be interpreted as a 'phase' of signals through the description of exemplary embodiments. Also, a relation between a positive polarity and a negative polarity of signals may be interpreted as a relation of a phase inversion/non-inversion of signals through the description of exemplary embodiments.

The methods and systems of the present invention are directed to insonifying ultrasound examinations using the contrast agents. In these examinations, the contrast agents are injected into the bloodstream of a patient. These contrast agents are largely composed of microbubbles and are chosen based on their ability to generate contrast echo signals over a relatively broad band of frequencies.

Figure 2:
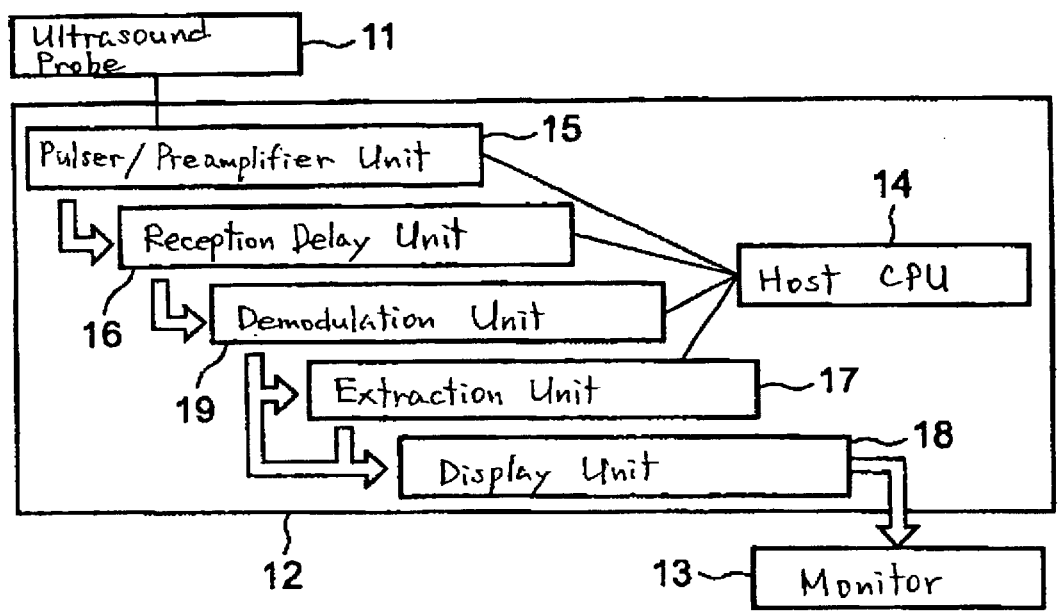
FIG. 2 is a block diagram illustrating an ultrasound diagnosis apparatus consistent with methods and systems of the present invention.
Figure 3:
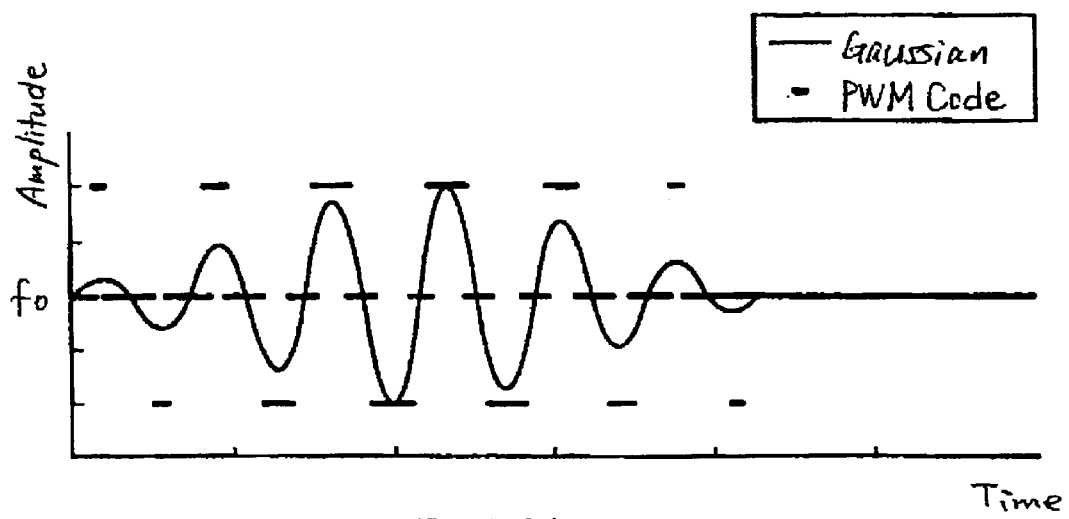
FIG. 3(a) is a graph illustrating transmission signals modulated by a duty ratio modulation consistent with methods and systems of the present invention.
FIG. 3(b) is a spectral graph illustrating a frequency spectrum of the transmission signals shown in FIG. 3(a) consistent with methods and systems of the present invention.
Figure 3:
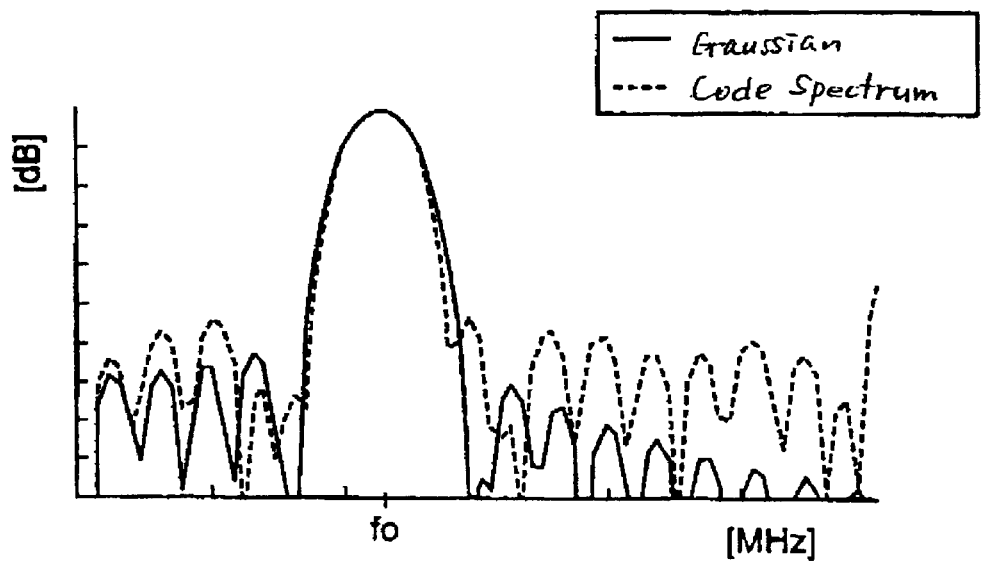

FIG. 2 is a block diagram illustrating an ultrasound diagnosis apparatus consistent with methods and systems of the present invention. The ultrasound diagnosis apparatus includes an ultrasound probe 11, a main body 12, and a monitor 13. The ultrasound probe 11 includes a plurality of vibration elements (not shown) such as conversion elements for converting between electrical signals and acoustical signals. The vibration elements are arranged in one-dimensional or two-dimensional arrays and typically produce a piezoelectric effect. The ultrasound probe 11 is connected to the main body 12 via one or more connectors (not shown).

Main body 12 may include a host central processing unit (CPU) 14, a pulser/preamplifier unit 15, a reception delay unit 16, an extraction unit 17 for extracting contrast agents echo signals, a display unit 18, and a demodulation unit 19. In an ultrasound diagnosis apparatus, one or more adjacent vibration elements may form a single channel. The embodiments of the present invention, however, will be explained such that one vibration element forms one channel.

Each vibration element of ultrasound probe 11 provides transmission signals (voltage pulses) of a relatively narrow frequency band (e.g., approximately 500 kHz or about 600 kHz with 6 [dB] down in both sides) centered about the fundamental frequency f0 (e.g., approximately 1.8 MHz when the frequency band is approximately 500 kHz, and approximately 2.0 MHz when the frequency band is approximately 600 kHz). The vibration elements of ultrasound probe 11 convert electrical vibration into mechanical vibration. Accordingly, ultrasound waves centered about the fundamental frequency f0 are generated from the vibration elements. Pulser/preamplifier unit 15 sets a time difference between channels (adjacent vibration elements) based to the time required for impressing the transmission signals. The time difference (delay time) is used to focus ultrasound waves generated from the plurality of vibration elements, and for deflecting the focused ultrasound waves. By changing the delay time, the ultrasound diagnostic system transforms a focal distance and a deflecting angle (transmission direction) of the focused ultrasound waves as needed.

Ultrasound probe 11 collects the return signals (echo signals) of transmitted ultrasound waves. These echo signals may include a fundamental echo component, a THI echo component, and a contrast echo component. The fundamental echo component originates from signal scattering resulting from the fundamental waves. The THI echo component originates from a nonlinear propagation of the fundamental waves in tissue. The contrast echo component originates from the contrast agents injected into the bloodstream of the specimen.

Ultrasound probe 11 sends the electrical signals generated by the vibration elements to demodulation unit 19 via pulse/preamplifier 15 and reception delay circuit 16. Demodulation unit 19 performs a quadrature demodulation on the electrical signals, and sends the demodulated signals to extraction unit 17. Alternatively, demodulation unit 19 may demodulate electrical signals sent from extraction unit 17.

Reception delay circuitry 16 performs a beam forming operation (phase adjusting and summing processing) on the electrical signals received from pulser/preamplifier unit 15, and controls the focal distance and the deflecting angle of the formed ultrasound beam. Reception delay circuitry 16 may comprise a plurality of a set of circuits (not shown) to simultaneously receive the electrical signals in parallel and produce a plurality of beams. Using at least the plurality set of circuits, reception delay circuitry 16 samples the received electrical signals with a sampling frequency appropriate for converting the electrical signals to digital signals. Reception delay circuitry 16 then forms the ultrasound beam based on the digital signals.

Demodulation unit 19 performs quadrature demodulation by multiplying signals received from reception delay circuitry 16 with signals of the reference frequency having a 90-degree phase difference from the phase of the received signals. Accordingly, demodulation unit 19 realizes I signals and Q signals as a result of the quadrature demodulation. In general, the reference frequency of demodulation unit 19 is set to a frequency centered about a frequency band comprising an ultrasound image. Demodulation unit 19 then sends the I signals and Q signals to extraction unit 17.

Extraction unit 17 receives the I signals and Q signals from demodulation unit 19. Extraction unit 17 extracts a frequency component from the I signals and Q signals. The extracted frequency component resides in a frequency band having a dominant contrast echo component as compared to the fundamental echo component and the THI echo component of the received signals. Extraction unit 17 provides the extracted frequency component on its output to display unit 18.

Display unit 18 generates an ultrasound diagnosis image data based on the frequency component output from extraction unit 17, and displays the prepared image data on monitor 13.

As discussed above, extraction unit 17 extracts a frequency component of a frequency band having a dominant contrast echo component. Extracting frequency components in this manner improves visibility of the contrast echo component and effectively enhances the contrast echo component without by preventing the contrast echo components from being buried in the received signal by the fundamental echo component and the THI echo component. As discussed in detail below, three types of signal processes may process extracted frequency components. Through CPU 14, an operator designates the type of processing executed at any one time and enables switching between any of the three processing types.

(First Embodiment)
[Phase Inversion Technique]

Transmission signals insonified to a specimen may include frequency signals ranged in a relatively narrow frequency band and centered about a fundamental frequency f0. The insonified transmission signals include signals having substantial transmission leakage (i.e., signals which do not include a lot of frequency components other than the fundamental frequency component). Insonified transmission signals, as described above, may be obtained by generating driven transmission signals via a linear amplifier (not shown). Alternatively, insonified transmission signals may also be generated via a duty ratio modulation technique, performed through a conventional switching pulser included in pulser/preamplifier unit 15.

Figure 3A:
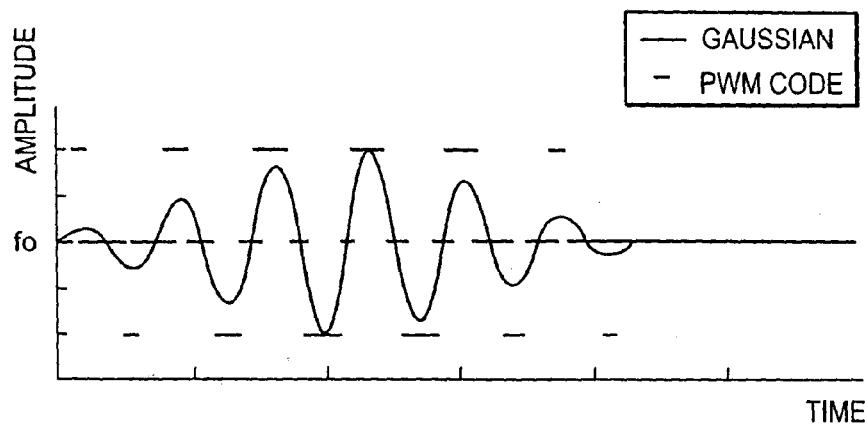
Figure 3B:
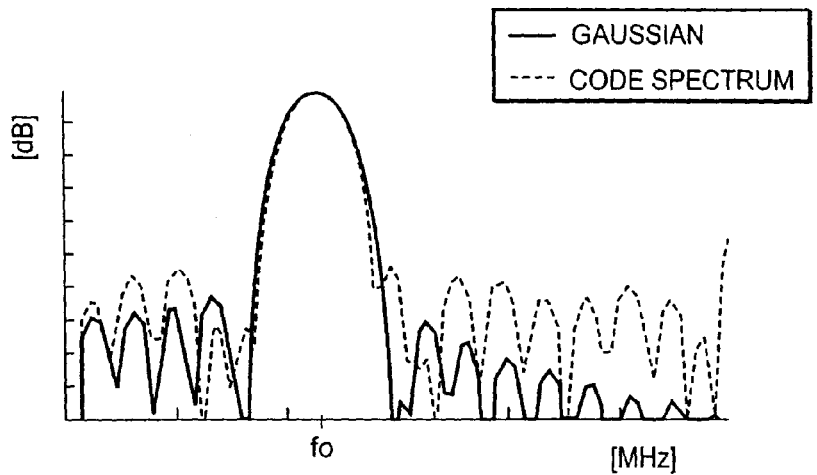
Figure 4A:
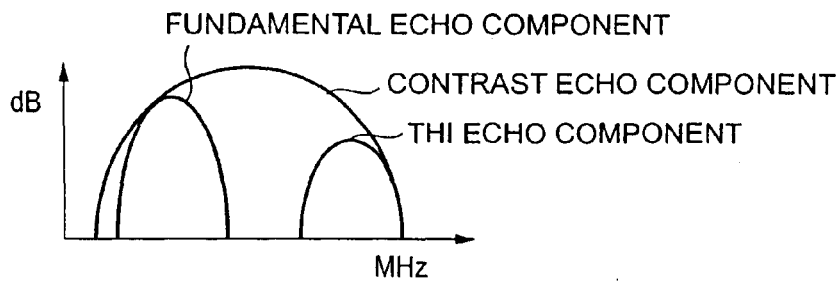
Figure 4B:
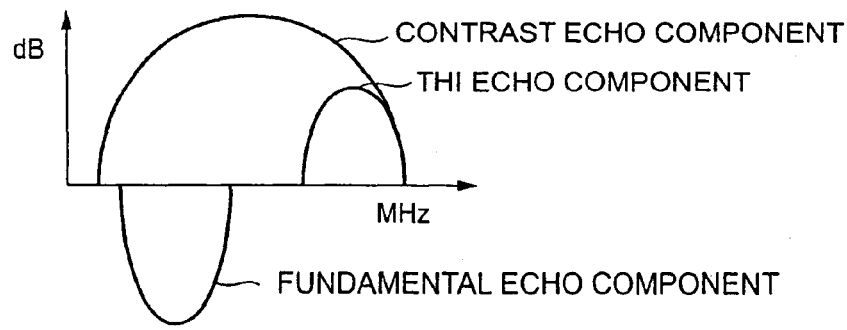
Figure 5:
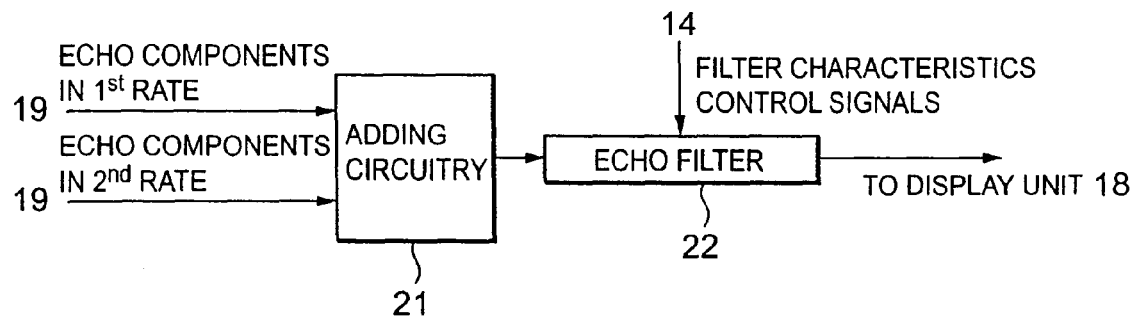
Figure 6:
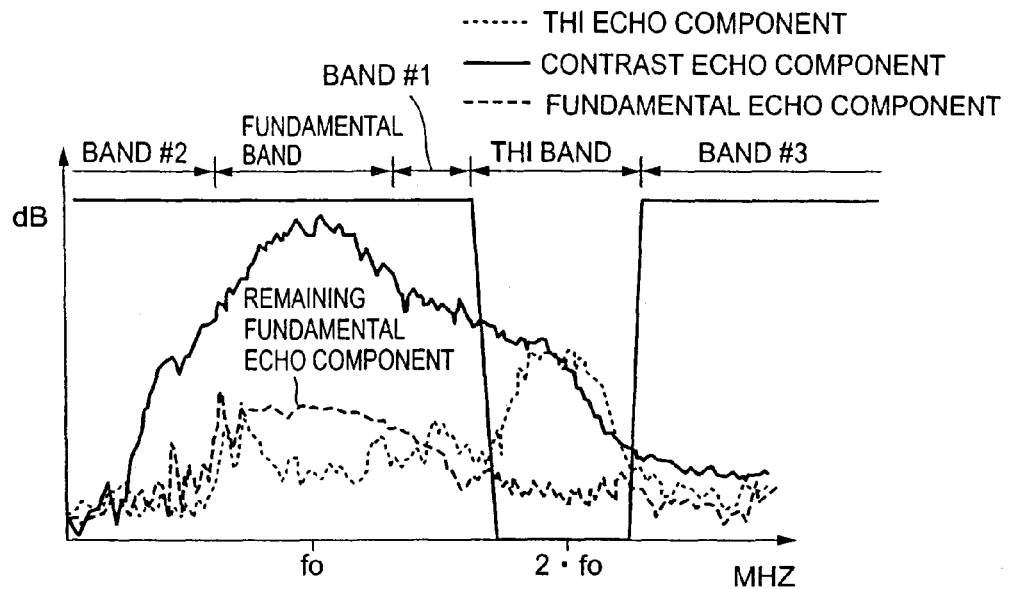
Figure 7:
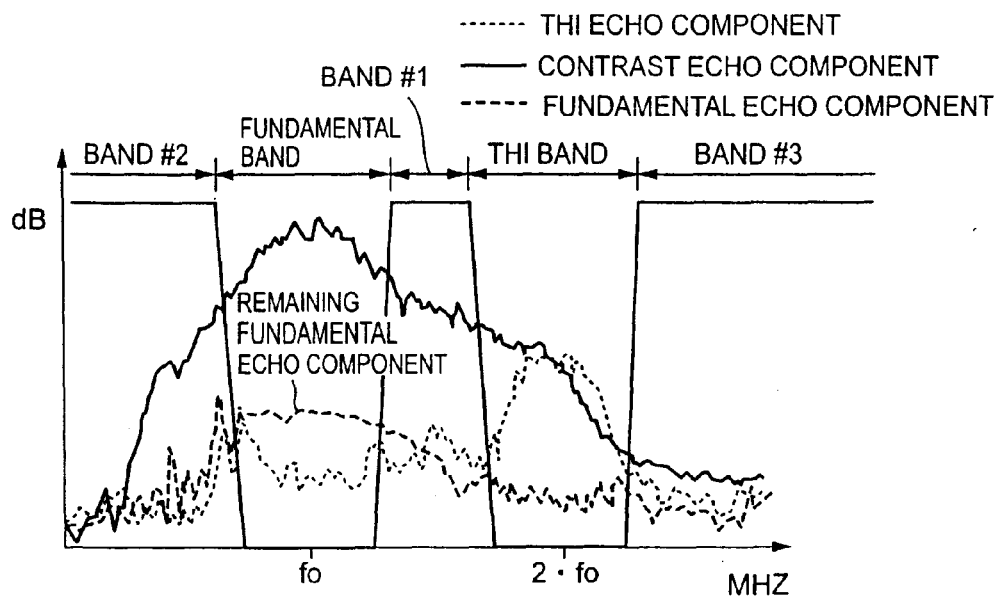
Figure 8:
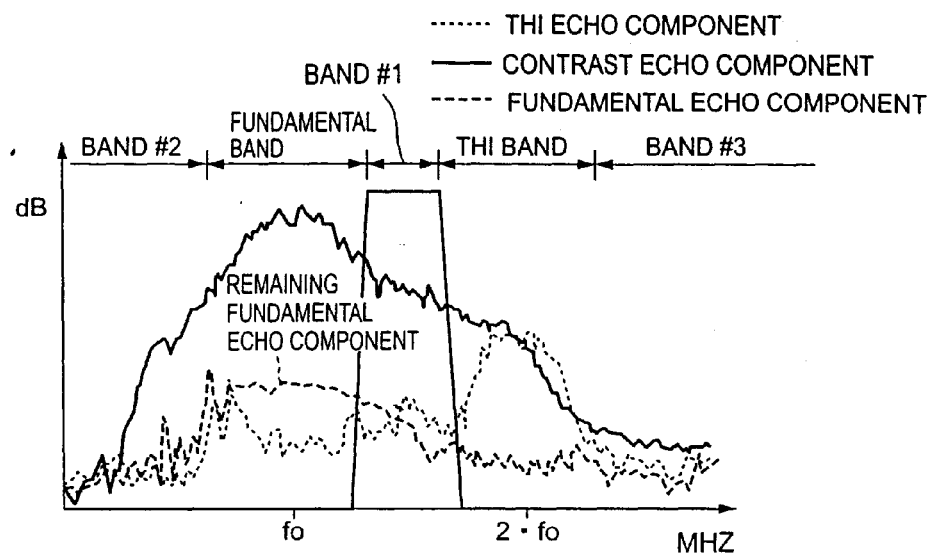
Figure 9A:
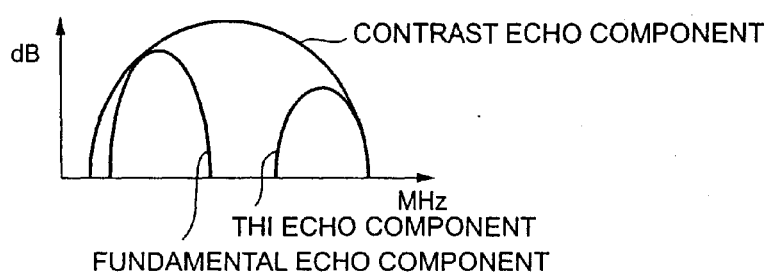
Figure 9B:
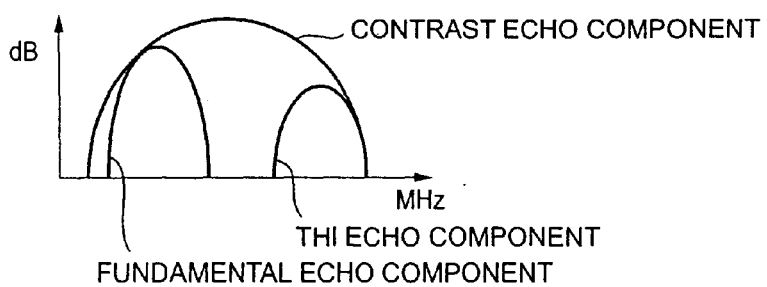
Figure 10:
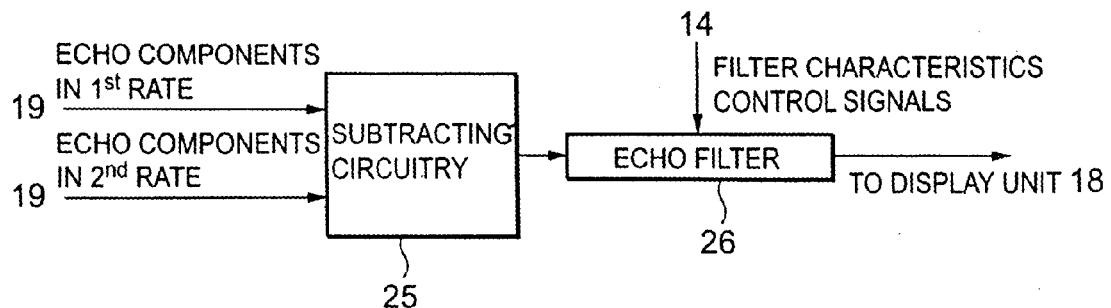
Figure 11:
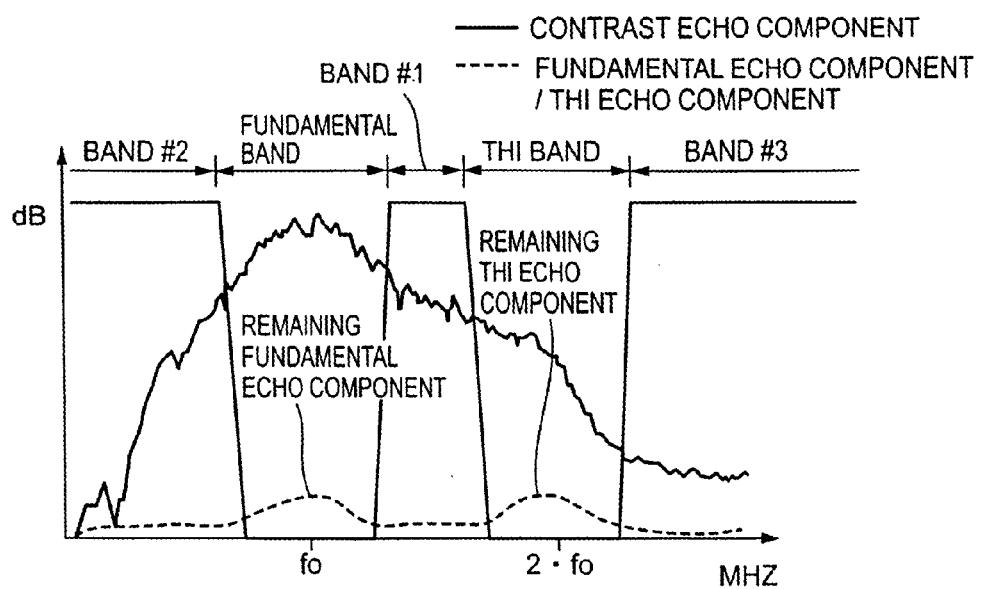
Figure 12:
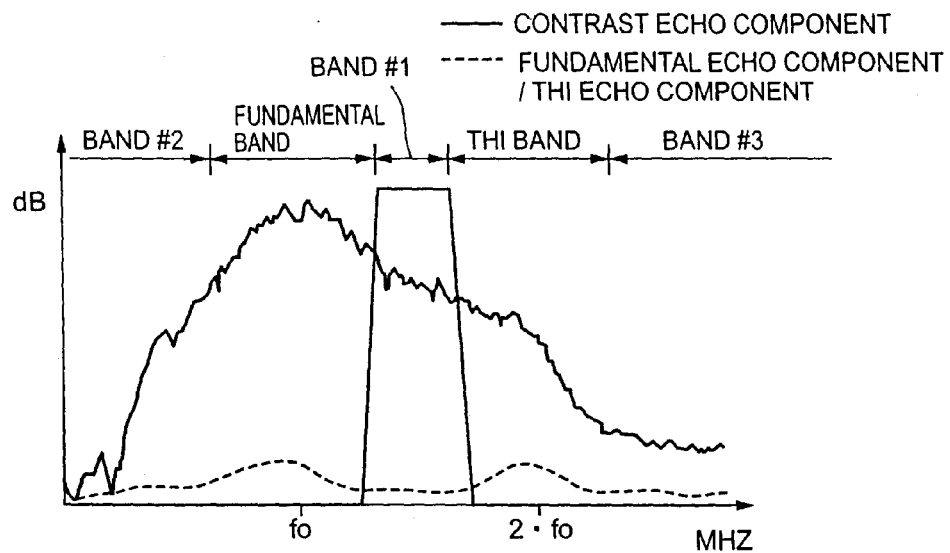
Figure 13:
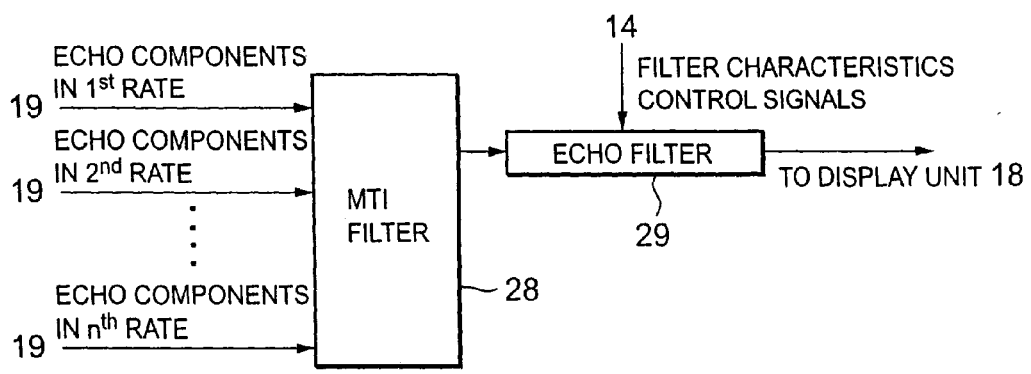

FIG. 3(a) is a graph illustrating transmission signals modulated by a duty ratio modulation having six burst waves consistent with systems and methods of the present invention. FIG. 3(b) is a spectral graph illustrating a frequency spectrum of the transmission signals shown in FIG. 3(a) consistent with methods and systems of the present invention. In a narrow frequency band, the number of transmitted burst waves may range between four and eight. In a first embodiment of the present invention, for example, six burst waves are transmitted in the narrow frequency band. When ultrasound waves lacking substantial transmission leakage are transmitted in a relatively narrow frequency band, both the fundamental echo component and the THI echo component of the ultrasound waves are less superposed on each other. Therefore, a frequency component between the fundamental echo component and the THI echo component is easily extracted when the contrast agents have been injected.

In a phase inversion technique consistent with the present invention, frequency band limited transmission signals are generated with at least two transmission rates. Further, each transmission rate includes transmission signals having a phase inversed 180 degrees (180 degrees phase difference). A THI echo component generated based on the band limited transmission signal has a same polarity (phase) regardless of between the transmission signals. The THI echo component has a positive polarity because of a nonlinearity of square. For example, when the fundamental echo component is represented as 'a(t)sin ωt' (1), its non-linear equivalent may be approximated as '$\alpha \cdot (\delta(a(t)\sin \omega t)^2/\delta t)$' (2). The THI echo component has a same (or an unique) polarity regardless of whether the transmission signals have a same polarity or an inversed polarity. On the other hand, the fundamental echo component is present in either a positive polarity or a negative polarity, based on the polarity of the transmission signals.

Figure 4A:
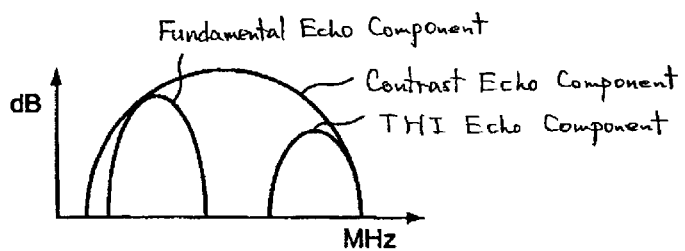
FIG. 4(a) is a simplified spectral graph illustrating components of received signals when transmission signals having a positive polarity are transmitted at a transmission rate consistent with methods and systems of the present invention.
Figure 4B:
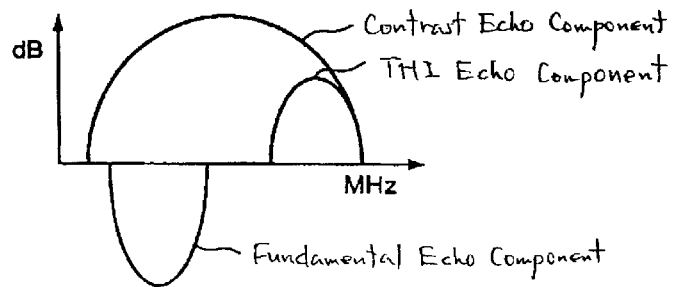
FIG. 4(b) is a simplified spectral graph illustrating components of the received signals when transmission signals having a negative polarity and are transmitted at a transmission rate consistent with methods and systems of the present invention.

FIG. 4(a) is a simplified spectral graph illustrating components of received signals when transmission signals are transmitted at a transmission rate consistent with methods and systems of the present invention. Further, FIG. 4(b) is a simplified spectral graph illustrating components of received signals when transmission signals which are phase inversed are transmitted at a transmission rate consistent with methods and systems of the present invention. In FIGS. 4(a) and 4(b), the contrast echo component and the THI echo component both have a same phase based on the transmission rate of the transmission signal having a positive polarity (the first transmission rate) and the transmission rate of the transmission signal having a negative polarity (the second transmission rate). In FIG. 4(a), the fundamental echo component has a positive polarity based on the transmission rate of a transmission signal having a positive polarity component of the received signal (the first transmission rate). In FIG. 4(b), the fundamental echo component has a negative polarity based on the transmission rate component of the received signal (the second transmission rate).

Figure 5:
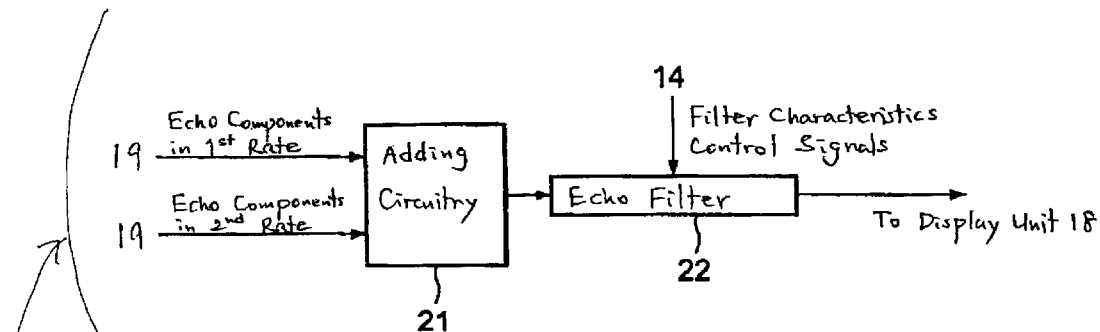
FIG. 5 is a block diagram illustrating an extraction unit for a phase inversion technique consistent with methods and systems of the present invention.

FIG. 5 is a block diagram illustrating extraction unit 17 for a phase inversion technique consistent with methods and systems of the present invention. Extraction unit 17 includes an adding circuitry 21 and an echo filter 22. As explained above, the fundamental echo component has a positive polarity based on the first transmission rate of the received signals and has a negative polarity based on the second transmission rate of the received signals based on the second transmission rate. Adding circuitry 21 removes the fundamental echo component from the received signals and maintains the contrast echo component and the THI echo component in the received signals. The fundamental echo component is removed by adding echo components of the received signals resulting from the transmission signals transmitted at the first rate and echo components of the received signals based on the transmission signals transmitted at the second rate.

The demodulation unit 19 may alternatively be provided physically or electrically between the adding circuitry 21 and the echo filter 22.

Figure 1:
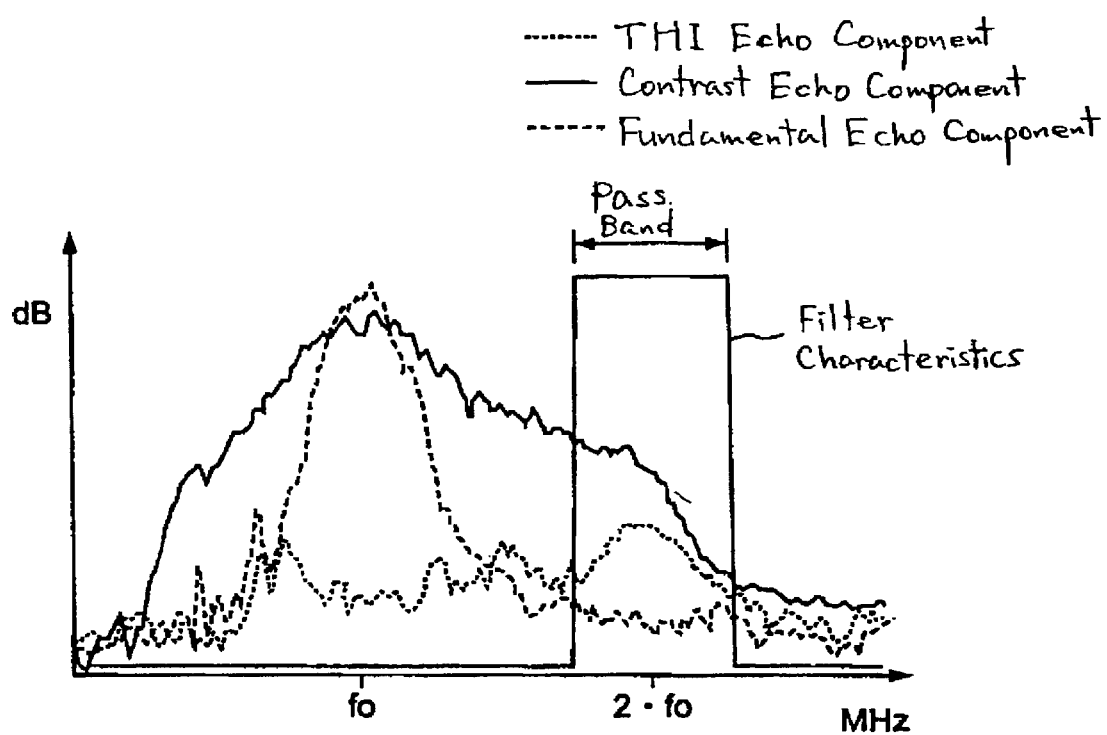
FIG. 1 is a spectral graph showing an example of components of received signals consistent with conventional methods and systems.
Figure 6:
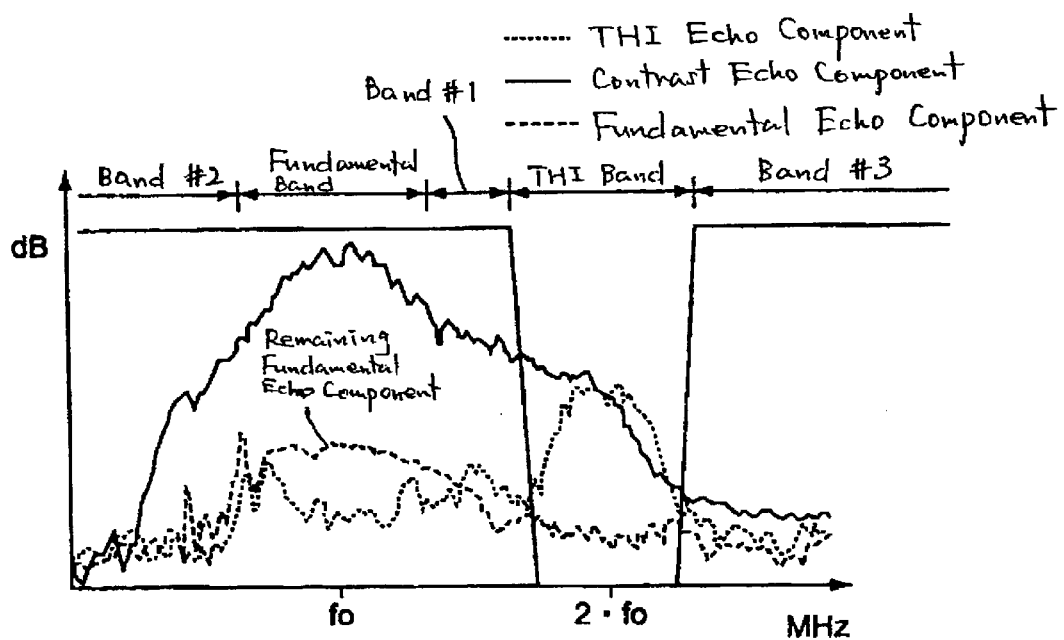
FIG. 6 is a spectral graph illustrating components of received signals filtered with first filter characteristics consistent with methods and systems of the present invention.

FIG. 6 is a spectral graph illustrating components of the received signals obtained from the adding circuitry 21 consistent with methods and systems of the present invention. In theory, as described above, the fundamental echo component can be removed in its entirety from the received signals. In practice, however, part of the fundamental echo component inevitably remains in the added signals due to movement of tissue in the specimen. The remaining fundamental echo component, however, is determined to be greatly reduced when compared to the fundamental echo component, as shown in FIG. 1.

The added signals output from adding circuitry 21 are provided to echo filter 22 in FIG. 5. A filter coefficient corresponding to an imaging mode of the ultrasound diagnosis apparatus is determined based on predetermined filter coefficients set for each imaging mode and responsive to the operator's selection of the imaging mode.

As shown in FIG. 6, the first filter characteristic of echo filter 22 suppresses a frequency band centered at approximately 2·f0, which is twice as high as the fundamental frequency f0 and having a dominant THI echo component. This frequency band is a THI band. In a frequency band lower than the THI band and a frequency band higher than the THI band, echo filter 22 does not suppress any components of the received signals.

It should be apparent that signals received after the quadrature demodulation processing may be signals of frequencies shifted with the reference frequency. Therefore, in practice, when echo filter 22 is used for the received signals after the quadrature demodulation processing of demodulation unit 19, an operator adjusts filter characteristics based on the frequency characteristics of the signals received after the quadrature demodulation processing of demodulation unit 19. For the purposes of this discussion, embodiments of the present invention are based on the frequency characteristics of the signals received before the quadrature demodulation processing of demodulation unit 17.

The above mentioned first filter characteristics may be advantageous in examinations of an abdomen of the specimen, because the abdomen usually has less movement when compared with other organs. As a result, only a small portion of the fundamental echo component remains in the filtered signals.

As described above, echo filter 22 suppresses the THI band of the received signals having first filter characteristics. In filtered signals, the contrast echo component may be the dominant echo component. When the contrast echo component of the filtered signals is the dominant echo component, visibility of the contrast echo component can be improved and the contrast echo component can be enhanced without burying the content of the contrast echo component beneath the fundamental echo component and the THI echo component.

Compared to the abdomen, circulatory organs of a specimen generally move more frequently. Thus, echo filter 22 having first filter characteristics cannot remove or effectively reduce the fundamental echo component in the received signal. This results in an appearance of a large portion of the remaining fundamental echo component in the filtered signals. As a result, second filter characteristics are applied to the echo filter 22.

Figure 7:
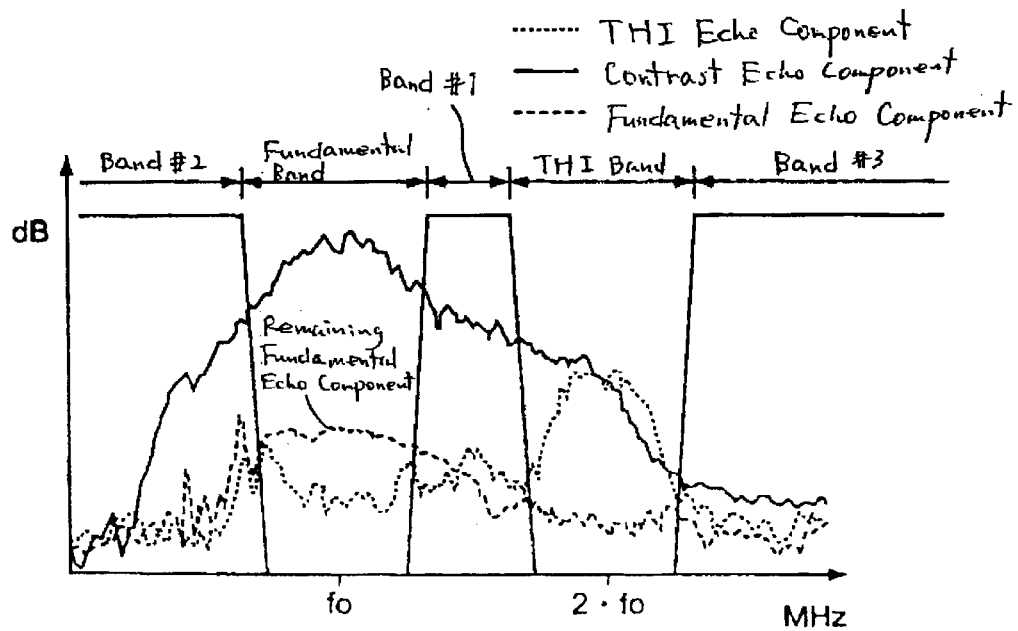
FIG. 7 is a spectral graph illustrating components of received signals filtered with second filter characteristics consistent with methods and systems of the present invention.

FIG. 7 is a spectral graph illustrating components of the received signals obtained from adding circuitry 21 when the received signals are filtered with a second filter characteristics consistent with methods and systems of the present invention. As shown in FIG. 7, the second filter characteristics of echo filter 22 suppresses the THI band centered about 2·f0 and a frequency band centered about f0. The frequency band centered about f0 is a fundamental band. In a first frequency band #1 centered about a frequency 1.5·f0 between the THI band and the fundamental band, for example, echo filter 22 does not suppress any components of the received signals. Furthermore, in a second frequency band #2 lower than the fundamental band, echo filter 22 does not suppress any components of the received signals. Still further, in a third frequency band #3 higher than the THI band, echo filter 22 does not suppress any components of the received signals.

Echo filter 22 suppresses the THI band and the fundamental band of the received signals with second filter characteristics. Regarding the filtered signals, the contrast echo component is more dominant. Therefore, when display unit 18 generates image data on the filtered signals of the second filter characteristic in an examination for the circulatory organs, improved visibility of the contrast echo component and an enhanced contrast echo component is realized without burying the contrast echo component beneath fundamental echo component and the THI echo component of the received signal.

According to the second filter characteristics, the received signals remain in the first, second, and third discrete bands #1, #2, #3. Among the first, second, and third bands #1, #2, #3, the contrast echo component is most dominant in the first band #1, which is between the THI band and the fundamental band. In some instances, only the received signals contained in the first band #1 are visualized, and as a result, the second and third bands #2, #3 are excluded. In such an event, third filter characteristics may be applied to the echo filter 22.

Figure 8:
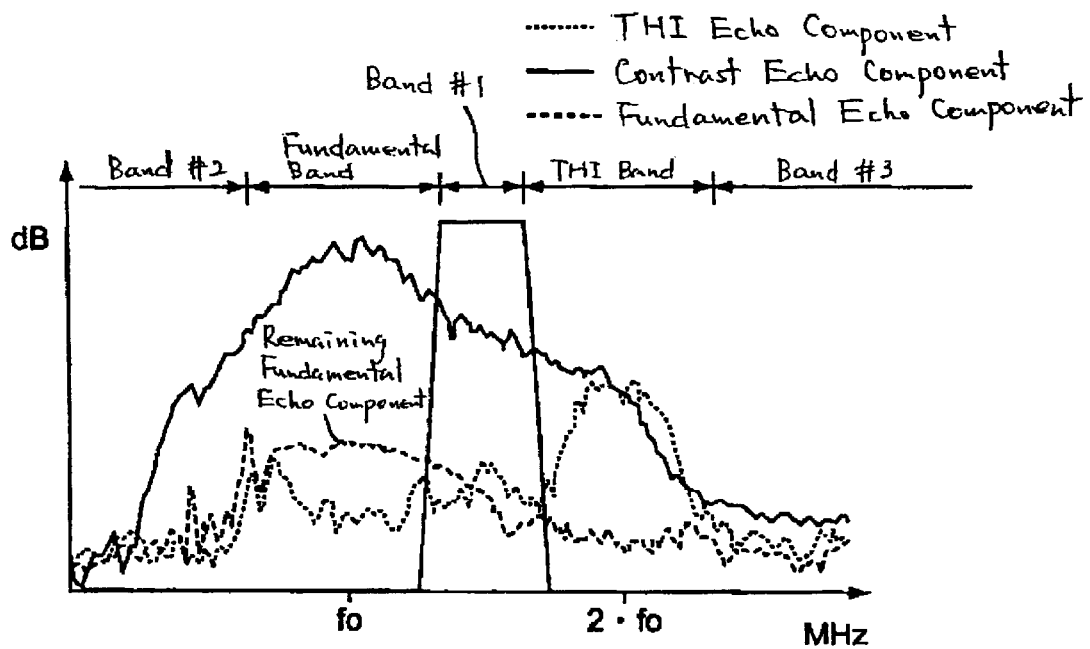
FIG. 8 is a spectral graph illustrating components of a received signal filtered with third filter characteristics consistent with methods and systems of the present invention.

FIG. 8 is a spectral graph illustrating components of the received signals obtained by adding circuitry 21 when filtered with third filter characteristics consistent with methods and systems of the present invention. As shown in FIG. 8, the third filter characteristics of echo filter 22 suppresses the THI band, the fundamental band, and the second and third bands #2, #3. In this instance, echo filter 22 does not suppress any components of the received signals included in the first frequency band #1.

Echo filter 22 suppresses the THI band, the fundamental band, and the second and third bands #2, #3 of the received signals with third filter characteristics. The filtered signals have frequencies higher than the second band #2 and accordingly have a higher lateral resolution. The filtered signals further include frequencies lower than the third band #3 and accordingly have better tissue penetration. As a result, when display unit 18 generates image data based on these filtered signals, improved visibility of the contrast echo component and an enhanced contrast echo component are realized without burying the contrast echo component beneath the fundamental echo component and the THI echo component.

(Second Embodiment)

[Subtraction Technique]

As discussed above regarding the phase inversion technique, transmission signals insonified into a specimen are signals of frequencies ranged in a relatively narrow frequency band centered about fundamental frequency f0. In a subtraction technique, however, frequency band limited transmission signals having the same polarity are transmitted with at least two transmission rates.

Figure 9A:
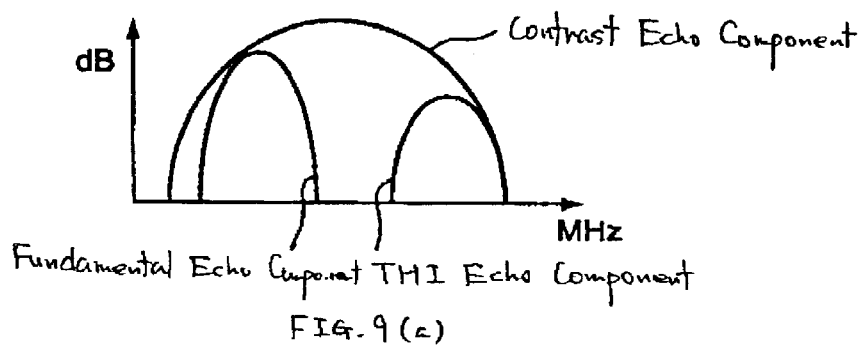
FIG. 9(a) is a simplified spectral graph illustrating components of received signals when transmission signals having a positive polarity are transmitted at a first transmission rate consistent with methods and systems of the present invention.
Figure 9B:
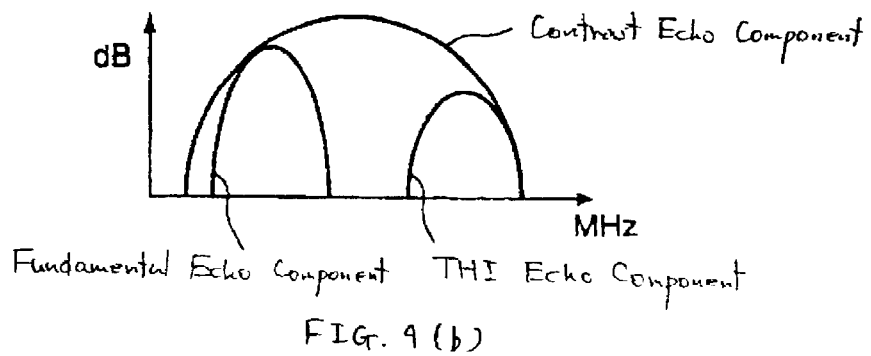
FIG. 9(b) is a simplified spectral graph illustrating components of received signals when transmission signals having a positive polarity are transmitted at a second transmission rate consistent with methods and systems of the present invention.

FIG. 9(a) is a simplified spectral graph illustrating components of received signals when the transmission signals are transmitted at a first transmission rate consistent with methods and systems of the present invention. Further, FIG. 9(b) is a simplified spectral graph illustrating components of received signals when the transmission signals have a same phase as the transmission signals transmitted at the first transmission rate and are sent at a second transmission rate consistent with methods and systems of the present invention. Therefore, as shown in FIGS. 9(a) and 9(b), the fundamental echo component, the THI echo component, and the contrast echo component have the same polarity as of the transmission signals (i.e. the same phase) transmitted at every transmission rate.

Figure 10:
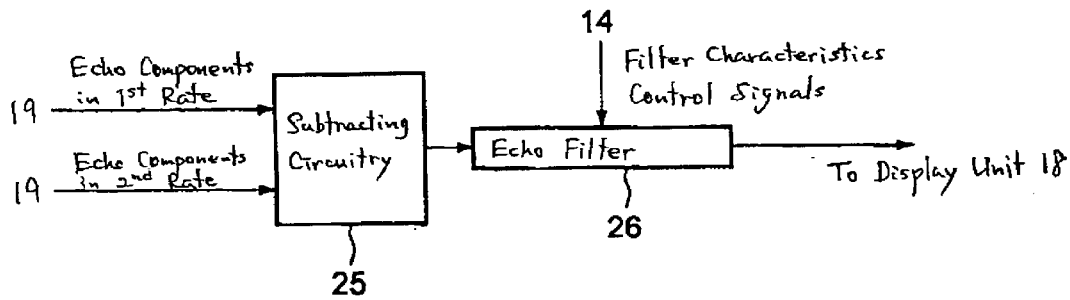
FIG. 10 is a block diagram illustrating an extraction unit for a subtraction technique consistent with methods and systems of the present invention.

FIG. 10 is a block diagram illustrating extraction unit 17 for performing a subtraction technique consistent with methods and systems of the present invention. Extraction unit 17 includes a subtracting circuitry 25 and an echo filter 26. Subtracting circuitry 25 sends output signals to echo filter 26. CPU 14 controls echo filter 26 by changing the filter characteristic control signals of echo filter 26 based on a designation of the operator. The filter coefficient of echo filter 26, which corresponds to an imaging mode of the ultrasound diagnosis apparatus, is determined based on predetermined filter coefficients set for each imaging mode and responsive to the operator's selection of the imaging mode.

As explained above, the fundamental echo component, the THI echo component, and the contrast echo component have a same polarity based on first and second transmission rates of the received signal. The fundamental echo component and the THI echo component are derived from tissue having insonified transmission signals. Because of the movement of the specimen's body, the fundamental and THI echo components are received with a time difference between the first and second transmission rates. The contrast echo component, on the other hand, is derived from the contrast agents. Because the contrast agents move with flow of blood, the signal difference between each transmission rate may be larger than that of the fundamental echo component and that of the THI echo component.

Therefore, when subtracting circuitry 25 subtracts echo components of the received signals resulting from the transmission signals transmitted at the first transmission rate from the echo components of the received signals resulting from the transmission signals transmitted at the second transmission rate, the fundamental echo component and the THI echo component can be greatly reduced. The remaining fundamental echo component and THI echo component are less than a remaining contrast echo component, and accordingly, the remaining contrast echo component is enhanced.

Figure 11:
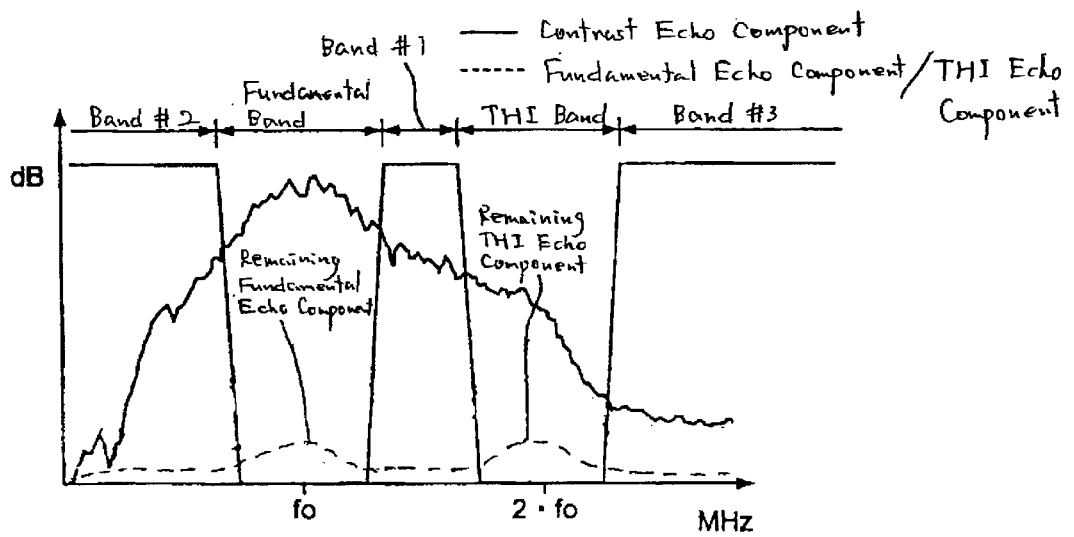
FIG. 11 is a spectral graph showing components of received signals to be filtered with second filter characteristics consistent with methods and systems of the present invention.

FIG. 11 is a spectral graph illustrating components of the received signals obtained from subtracting circuitry 25 consistent with methods and systems of the present invention.

As shown in FIG. 11, in a first frequency band #1 located between the THI band and the fundamental band, when the second filter characteristics are applied to echo filter 26, the second filter characteristics of echo filter 26 suppresses the THI band centered about 2·f0 and the fundamental band centered about f0. Furthermore, echo filter 26 does not suppress any components of the received signals in a second frequency band #2, which is lower than the fundamental band. Still further, in a third frequency band #3, which is higher than the THI band, echo filter 26 does not suppress any components of received signals.

Figure 12:
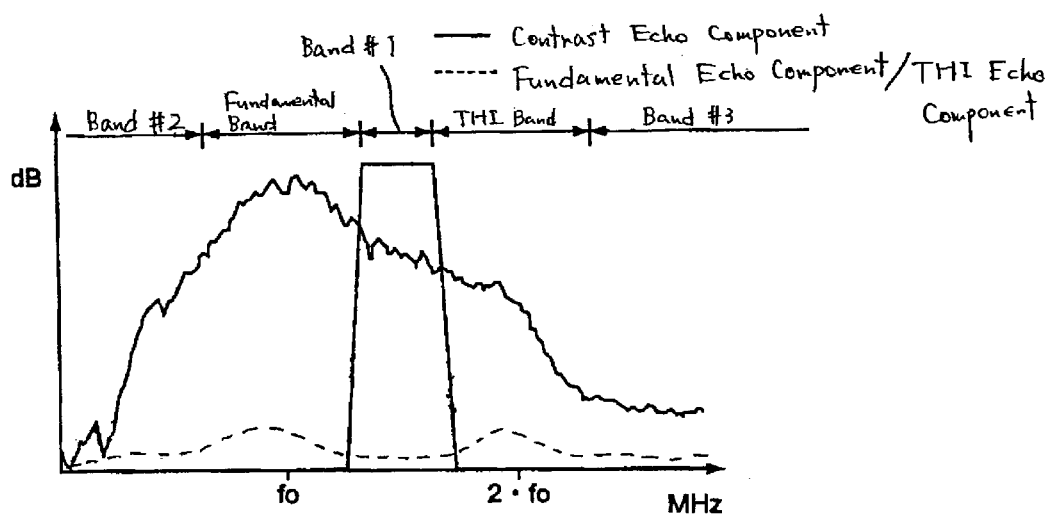
FIG. 12 is a spectral graph illustrating components of received signals that will be filtered with third filter characteristics consistent with methods and systems of the present invention.

FIG. 12 is a spectral graph illustrating components of the received signals obtained via subtracting circuitry 25 when the received signals are filtered with third filter characteristics consistent with methods and systems of the present invention. In FIG. 12, using the third filter characteristics, echo filter 26 suppresses the THI band, the fundamental band, and second and third bands #2, #3. Echo filter 26 maintains all components of the received signals in the first frequency band #1 without suppression.

As a result, visibility of the contrast echo component and enhancement of the contrast echo component are realized without being buried by the fundamental echo component and the THI component. Realization is achieved by selectively using the second filter characteristics and the third filter characteristics based on an examination of the specimen, when display unit 18 generates image data based on the received signals filtered with selected filter characteristics.

(Third Embodiment)
[Doppler Technique]

Under the phase inversion technique, as discussed above, transmission signals to be insonified to the specimen may be signals having frequencies located in a relatively narrow frequency band centered about the fundamental frequency f0. A linear amplifier driving or a switching pulse may return to the duty ratio modulation technique to obtain such transmission signals. In each of the transmission rates, the polarity of the transmission signals may be the same. Alternatively, the transmission signals may include both a positive polarity component and the negative polarity component, either of which depends on each of the rates. Further, the transmission signals may be transmitted in four transmission rates or in an integral multiple number of transmission rates, where transmission signals of the four transmission rates can have a 90-degree difference among them.

Figure 13:
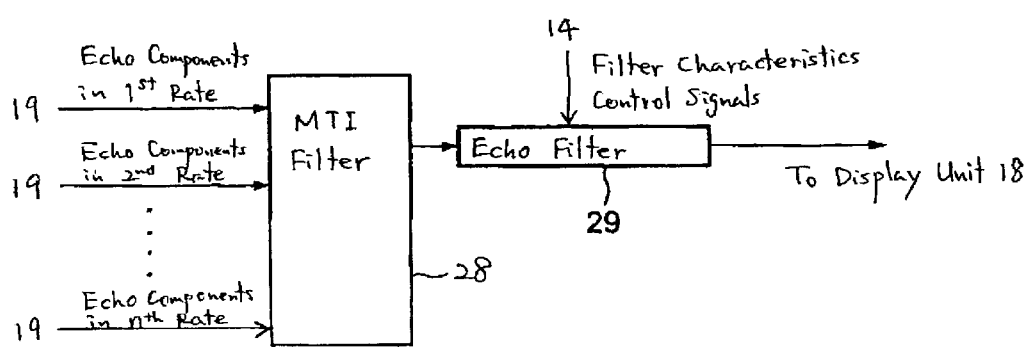
FIG. 13 is a block diagram illustrating an extraction unit for a Doppler technique consistent with methods and systems of the present invention.
Figure 14:
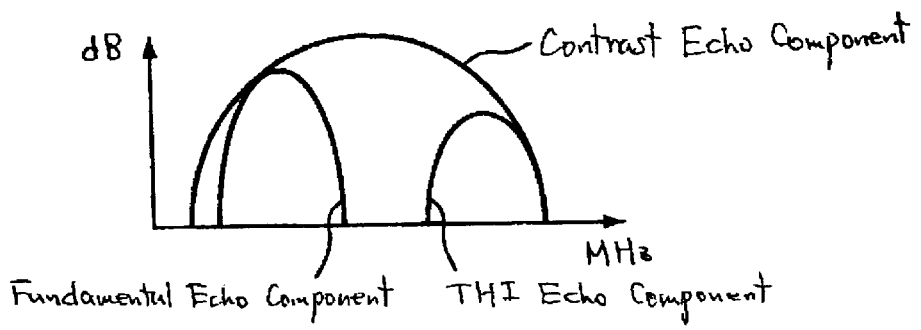
FIG. 14(a) is a simplified spectral graph illustrating components of received signals consistent with methods and systems of the present invention.
FIG. 14(b) is a simplified spectral graph illustrating components of received signals when the received signals are filtered by a moving target indicator (MTI) filter consistent with methods and systems of the present invention.
Figure 14:
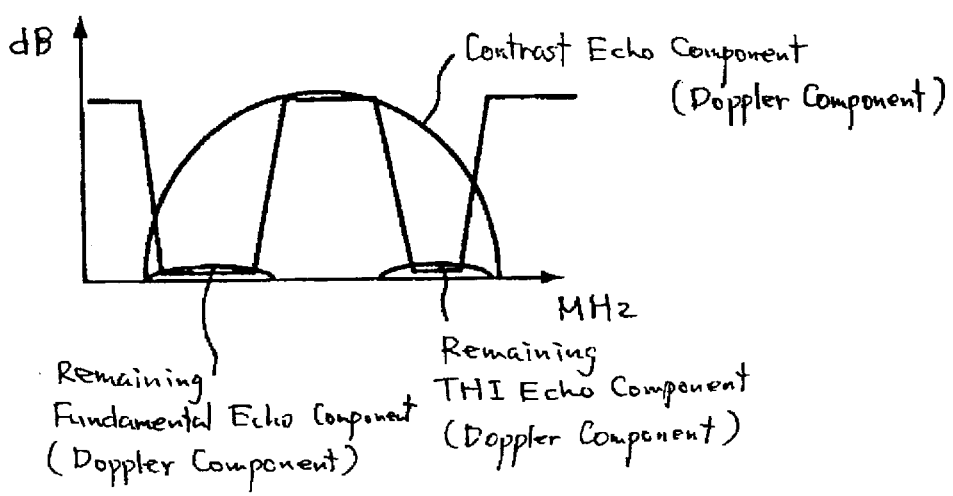
Figure 15:
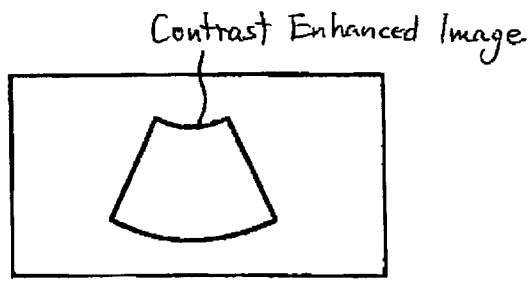
FIG. 15(a) is an illustration of a first example of an image display consistent with methods and systems of the present invention.
FIG. 15(b) is an illustration of a second example of an image display consistent with methods and systems of the present invention.
FIG. 15(c) is an illustration of a third example of an image display consistent with methods and systems of the present invention.
Figure 15:
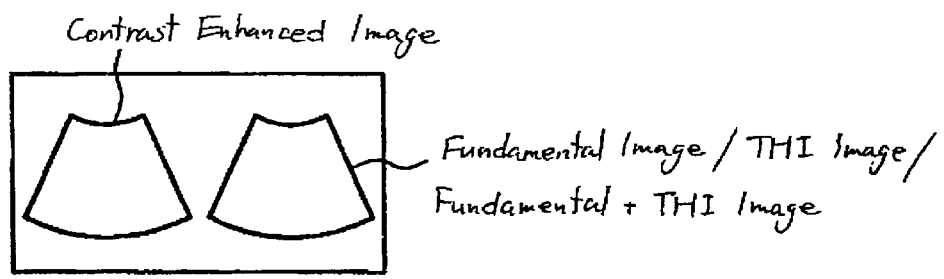
Figure 15:
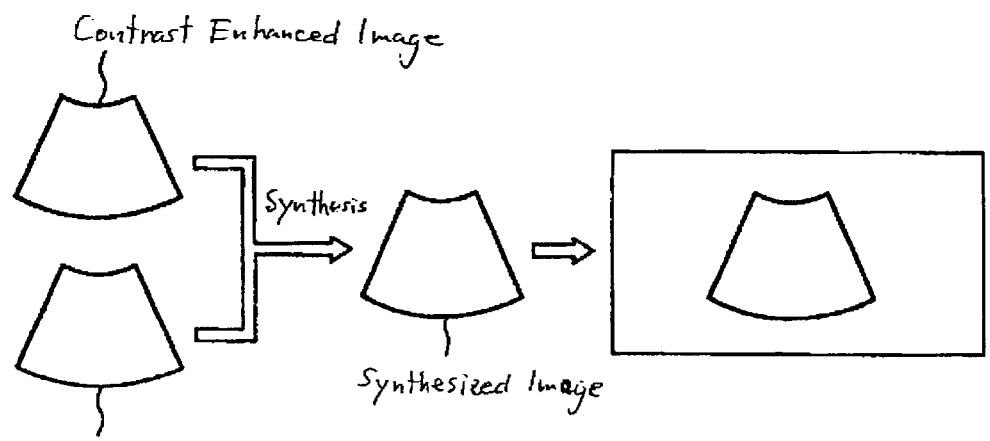
Figure 1:
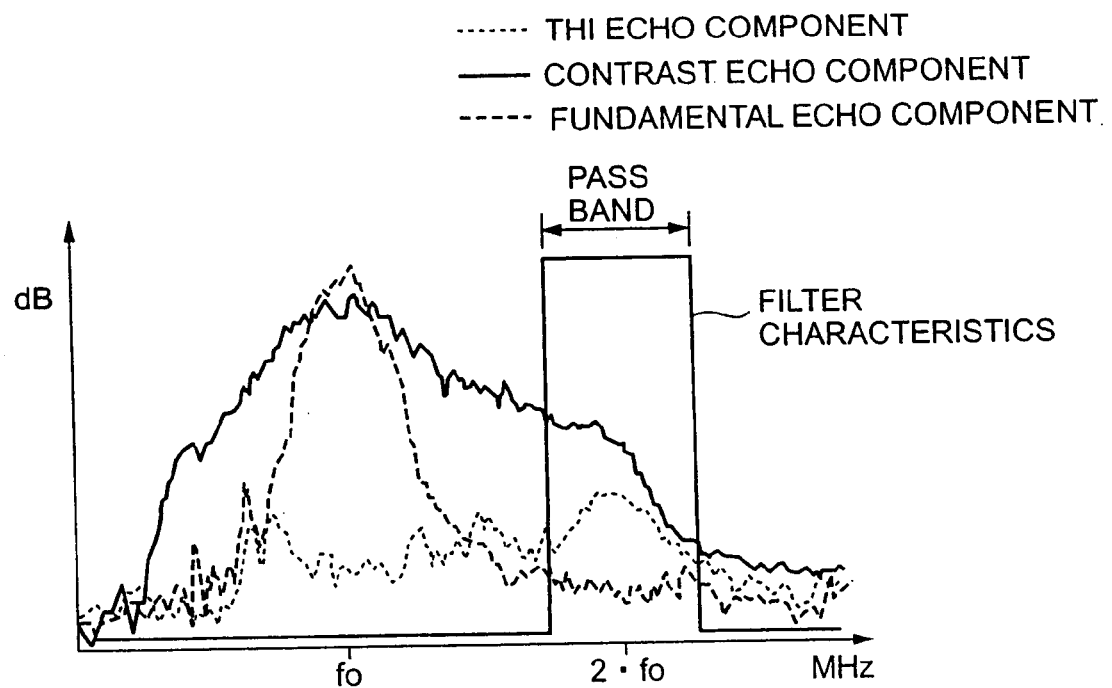
Figure 2:
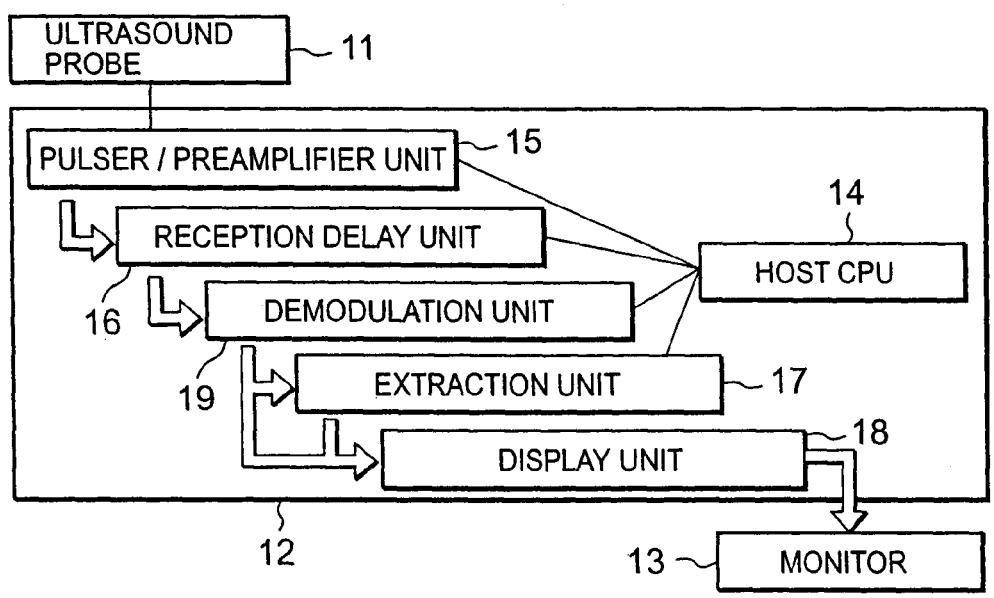

FIG. 13 is a block diagram illustrating extraction unit 17 for a Doppler technique consistent with methods and systems of the present invention. Extraction unit 17 includes an MTI filter 28 and an echo filter 29.

MTI filter 28 provides the filtered signals on its output to echo filter 29. CPU 14 controls echo filter 29 via filter characteristics control signals, which are responsive to an input of the operator. Filter coefficients, for example, are predetermined and set for each imaging mode of the ultrasound diagnosis apparatus. Moreover, echo filter 29 determines a filter coefficient based on an operator's image mode selection. In a third embodiment of the present invention, the filter coefficients may be used in a first filter characteristics, second filter characteristics, and third filter characteristics, as described above.

Figure 14A:
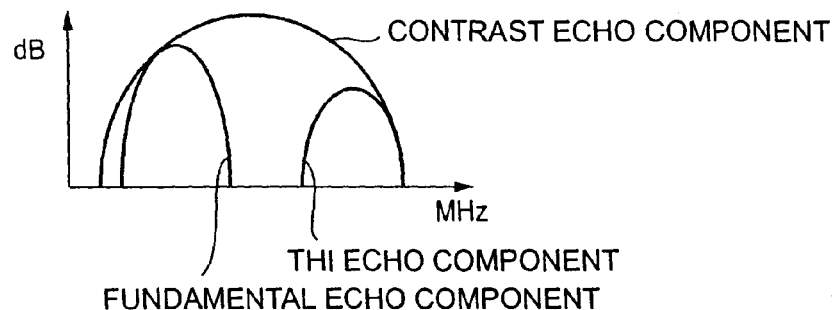
Figure 14B:
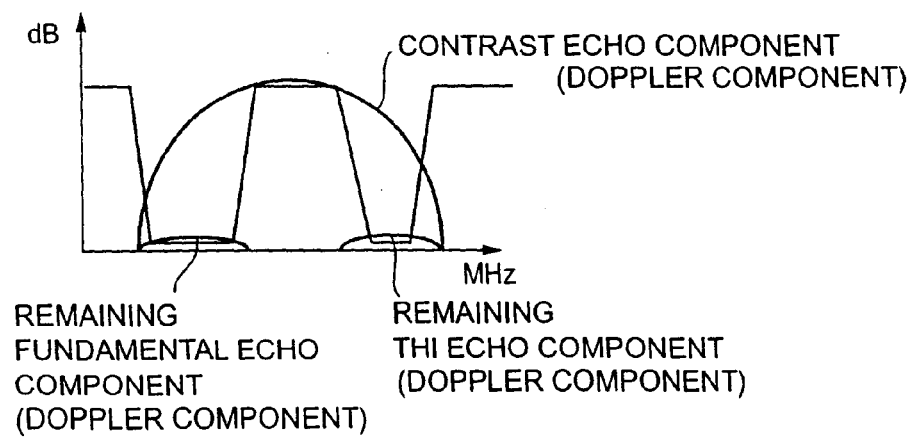

FIG. 14(a) is a simplified spectral graph illustrating echo components of received signals consistent with methods and systems of the present invention. FIG. 14(b) is a simplified spectral graph illustrating echo components of received signals when the received signals are filtered by an MTI (moving target indicator) filter consistent with methods and systems of the present invention.

In FIG. 14(a), the contrast echo component, fundamental echo component, and THI echo component are received with the same polarity when the transmission signals are transmitted with the same polarity at each of the four transmission rates. In FIG. 14(b), MTI filter 28 extracts most of the contrast echo component of received signals when the transmission signals are transmitted with the same polarity at each of the four transmission rates. This extraction occurs because the contrast agents move with the flow of blood. MTI filter 28 also removes or suppresses a majority of the fundamental echo component and the THI echo component because both echo components are transmitted with a time difference in accordance with movement of the specimen's body.

Furthermore, MTI filter 28 may extract most of the contrast echo component when the transmission signals are transmitted with at least one of an original polarity and a phase inversed polarity. This extraction occurs because contrast agents move with the flow of blood. Alternatively, MTI filter 28 may remove or suppress a majority of the fundamental echo component and the THI echo component because both of these echo components are transmitted with a time difference between the four transmission rates in accordance with the movement of the specimen's body.

As a result, embodiments consistent with the present invention realize visibility of the contrast echo component and an enhanced echo component when display unit 18 generates image data based on received signals filtered with at least one of the first, second, or third filter characteristics. Moreover, the improved visibility and enhancement of the echo component are achieved without the contrast echo component being buried by the fundamental echo component and the THI echo component.

Furthermore, additional processing of the echo components removes or reduces the fundamental echo component and the THI echo component when the transmission signals are transmitted at four transmission rates or an integral multiple of transmission rates with a 90-degree phase difference between the signals.

Figure 15A:
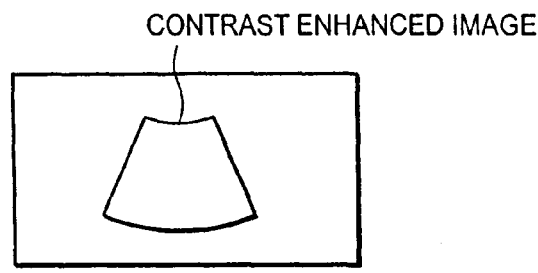
Figure 15B:
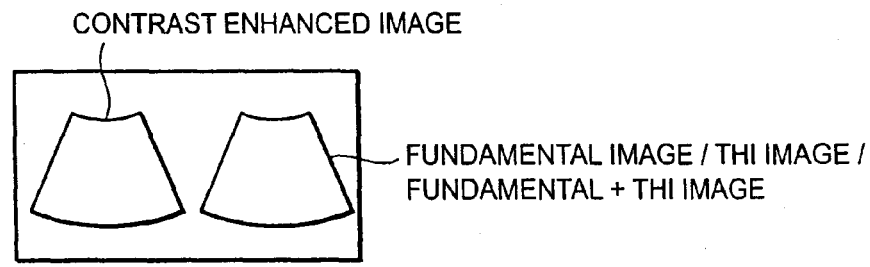
Figure 15C:
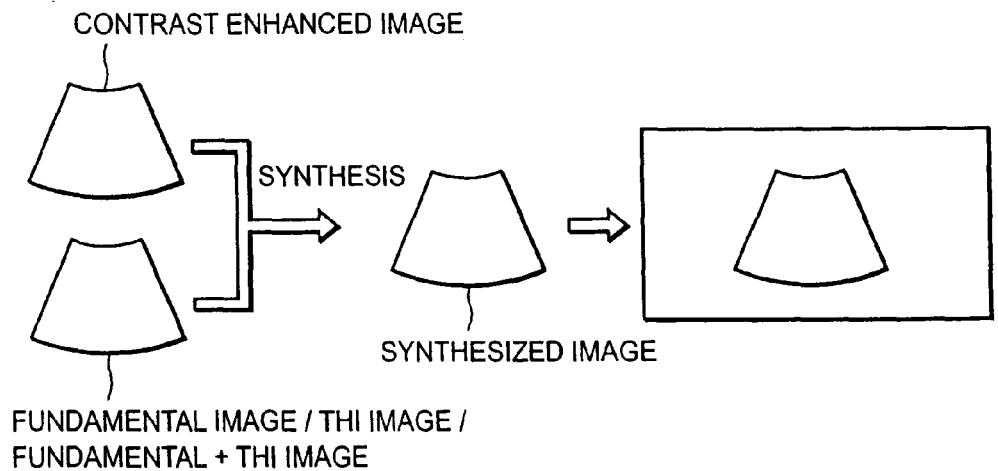

FIGS. 15(a) to (c) illustrate examples of displaying images including a contrast enhanced image obtained by one of the techniques consistent with methods and systems of the present invention.

Display unit 18 prepares image data (contrast enhanced image data) based on the contrast echo component extracted or enhanced by one of the phase inversion, subtraction, or Doppler techniques described above. Furthermore, display unit 18 develops the prepared image data by converting the image data. Display unit 18 further stores in memory a lookup table associated with gray scaled image data/colored image data. Monitor 13 displays the developed image data (the contrast enhanced image data) in a manner shown in FIG. 15(a).

In another example, and as shown in FIG. 15(b), monitor 13 displays in parallel the contrast enhanced image in color (or in a gray scale) and another image in a gray scale, respectively. The colored contrast enhanced image of FIG. 15(b) is obtained in the same manner as described with respect to FIG. 15(a). The other image displayed with the contrast enhanced image is obtained by processing the received signals used for acquiring the contrast enhanced image. These received signals have transmission rates different from those used for the contrast enhanced image. Extraction unit 17 extracts at least one of a component of the fundamental band and a component of the THI band from these received signals. Display unit 18 generates image data in a manner described above based on the at least one component extracted by extraction unit 17. The other image may be a fundamental image, a THI image, or combination of a fundamental and THI image including the fundamental band component and the THI band component.

In another example, as shown in FIG. 15(c), monitor 13 displays the contrast enhanced image and the other image described above as a single synthesized image. Monitor 13 displays the contrast enhanced image portion of the synthesized image in color or in gray scale, and displays the other image part of the synthesized image in gray scale.

In each of the above examples, the signal intensity of the received signals is improved because the filtered signals comprise at least two frequency bands of the fundamental frequency band, and first, second, and third frequency bands #1, #2, #3.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

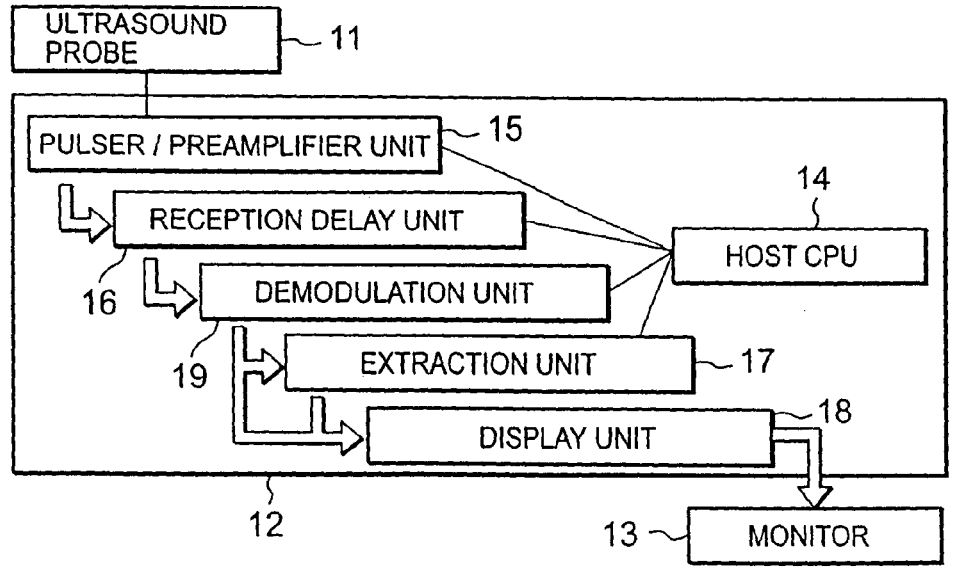

What is claimed is:

1. An ultrasound diagnosis apparatus for imaging with a contrast agent, comprising:
    a transceiver unit for insonifying an object injected with a contrast agent via an ultrasound transmission signal transmitted at a fundamental frequency f0 with at least two transmission rates and receiving an ultrasound echo signal from the object based on the ultrasound transmission signal, wherein polarities of the ultrasound transmission signal are alternately inversed;
    an adding processor for adding a first component and a second component of the ultrasound echo signal, wherein the first component is received by the transceiver unit at a first rate of the at least two transmission rates and the second component is received by the transceiver unit at a second rate of the at least two transmission rates;
    a filter for suppressing at least a first frequency band of an addition result that is centered about a frequency 2·f0; and
    an image processor for generating first image data based on a suppressing result.

2. The apparatus of claim 1, wherein the filter suppresses a second frequency band centered about the fundamental frequency f0.

3. The apparatus of claim 2, wherein the filter suppresses a third frequency band lower than the second frequency band and a fourth frequency band higher than the first frequency band.

4. The apparatus of claim 1, wherein the filter suppresses another frequency band centered about a frequency n·f0, wherein n is a positive integer.

5. The apparatus of claim 1, wherein the filter suppresses another frequency band other than a frequency band centered about a frequency 1.5·f0.

6. The apparatus of claim 1, wherein the first component of the ultrasound echo signal comprises a first fundamental echo component, a first tissue harmonic imaging echo component, and a first contrast agent echo component, and wherein the second component of the ultrasound echo signal comprises a second fundamental echo component, a second tissue harmonic imaging echo component, and a second contrast agent echo component.

7. The apparatus of claim 1, further comprising a display configured to display the image data produced by the image processor.

8. The apparatus of claim 7, further comprising an extracting processor for extracting, from the ultrasound echo signal, at least one of a second frequency band component centered about the fundamental frequency f0 and a third frequency band component centered about the frequency 2·f0, wherein the image processor generates second image data based on at least one of the components extracted by the extracting processor, and the display displays the second image data with the first image data.

9. The apparatus of claim 8, wherein the image processor produces the second image data, which synthesizes the second frequency band component and the third frequency band component, when the extracting processor extracts the second frequency band component and the third frequency band component.

10. The apparatus of claim 7, further comprising an extracting processor for extracting, from the ultrasound echo signal, at least one of a second frequency band component centered about the fundamental frequency f0 and a third frequency band component centered about the frequency 2·f0, wherein the image processor synthesizes at least one of the components extracted by the extracting processor with the first image data, and wherein the display displays the synthesized image data.

11. A method of imaging with a contrast agent in an ultrasound diagnosis apparatus, comprising:
    insonifying an object injected with a contrast agent via an ultrasound transmission signal transmitted at a fundamental frequency f0 with at least two transmission rates, wherein polarities of the ultrasound transmission signal are alternately inversed;
    receiving an ultrasound echo signal from the object based on the ultrasound transmission signal;
    adding a first component and a second component of the received ultrasound echo signal, wherein the first component is received at a first rate of the at least two transmission rates and the second component is received at a second rate of the at least two transmission rates;
    suppressing at least a first frequency band of an addition result that is centered about a frequency 2·f0; and
    generating image data based on a suppressing result.

12. An ultrasound diagnosis apparatus for imaging with a contrast agent, comprising:
    a transceiver unit for insonifying an object injected with a contrast agent via an ultrasound transmission signal transmitted at a fundamental frequency f0 with at least two transmission rates and receiving from the object an ultrasound echo signal based on the ultrasound transmission signal, wherein the ultrasound transmission signal has a similar wave profile among the at least two transmission rates;
    a subtracting processor for subtracting a first component of the ultrasound echo signal from a second component of the ultrasound echo signal, wherein the first component is received at a first rate of the at least two transmission rates and the second component is received at a second rate of the at least two transmission rates;
    a filter for suppressing a frequency band of a subtraction result that is centered about a frequency n·f0, wherein n is a positive integer; and
    an image processor for generating image data based on a suppressing result.

13. The apparatus of claim 12, wherein the filter suppresses a second frequency band lower than the frequency band centered about a frequency f0 and a third frequency band higher than the frequency band centered about a frequency 2·f0.

14. A method of imaging with a contrast agent in an ultrasound diagnosis apparatus, comprising:

insonifying an object injected with a contrast agent via an ultrasound transmission signal transmitted at a fundamental frequency f0 with at least two transmission rates, wherein the ultrasound transmission signal has a similar wave profile among the at least two transmission rates;

receiving from the object an ultrasound echo signal based on the ultrasound transmission signal;

subtracting a first component of the ultrasound echo signal from a second component of the ultrasound echo signal, wherein the first component is received at a first rate of the at least two transmission rates and the second component is received at a second rate of the at least two transmission rates;

suppressing a frequency band of a subtraction result that is centered about a frequency n·f0, wherein n is a positive integer; and generating image data based on a suppressing result.

15. An ultrasound diagnosis apparatus for imaging with a contrast agent, comprising:

a transceiver unit for insonifying an object injected with a contrast agent via an ultrasound transmission signal transmitted at a fundamental frequency f0, and receiving an ultrasound echo signal from the object based on the ultrasound transmission signal;

a moving target indication processor for extracting a component of the ultrasound echo signal based on the transmission signal received by the transceiver unit from a moving target of the object;

a filter for suppressing a frequency band of the ultrasound echo signal centered about a frequency n·f0, wherein n is a positive integer greater than or equal to 2; and an image processor for generating image data based on a suppressing result.

16. The apparatus according to claim 15, wherein the filter suppresses a second frequency band centered about a frequency f0.

17. A method of imaging with a contrast agent in an ultrasound diagnosis apparatus, comprising:

insonifying an object injected with a contrast agent via an ultrasound transmission signal transmitted at a fundamental frequency f0;

receiving from the object an ultrasound echo signal based on the ultrasound transmission signal;

extracting a component of the received ultrasound echo signal from a moving target of the object;

suppressing a frequency band of an extracting result that is centered about a frequency n·f0, wherein n is a positive integer greater than or equal to 2; and generating image data based on a suppressing result.

18. The method according to claim 17, further comprising suppressing a second frequency band centered about a frequency f0.

19. An ultrasound diagnosis apparatus for imaging with a contrast agent, comprising:

a transceiver unit for insonifying an object injected with a contrast agent via an ultrasound transmission signal transmitted at a fundamental frequency f0, and receiving from the object an ultrasound echo signal based on the ultrasound transmission signal;

a reduction processor for reducing at least a fundamental echo component of the ultrasound echo signal;

a filter for suppressing a frequency band of a reduction result that is centered about a frequency n·f0, wherein n is a positive integer greater than or equal to 2; and an image processor for generating image data based on a suppressing result.

20. The apparatus according to claim 19, wherein the filter suppresses a second frequency band centered about a frequency f0.

* * * * *

UNITED STATES PATENT AND TRADEMARK OFFICE
CERTIFICATE OF CORRECTION

PATENT NO. : 6,726,630 B2
DATED : April 27, 2004
INVENTOR(S) : Tetsuya Kawagishi It is certified that error appears in the above-identified patent and that said Letters Patent is hereby corrected as shown below:

Drawings,
Please replace Figures 1-15(c) with the attached 10 replacement figure sheets.

Signed and Sealed this

Seventh Day of September, 2004

JON W. DUDAS
*Director of the United States Patent and Trademark Office*

(12) United States Patent
Kawagishi

(10) Patent No.: US 6,726,630 B2
(45) Date of Patent: Apr. 27, 2004

(54) ULTRASOUND DIAGNOSIS APPARATUS FOR IMAGING WITH A CONTRAST AGENT

(75) Inventor: Tetsuya Kawagishi, Tochigi-ken (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 10/290,147

(22) Filed: Nov. 8, 2002

(65) Prior Publication Data
US 2003/0092992 A1 May 15, 2003

(30) Foreign Application Priority Data
Nov. 8, 2001 (JP) ........................... 2001-343577

(51) Int. Cl.[7] ................................................ A61B 8/14
(52) U.S. Cl. ................................................... 600/458
(58) Field of Search ............................. 600/407–471; 73/620–633; 367/2, 11, 130, 138; 128/916

(56) References Cited

U.S. PATENT DOCUMENTS 5,980,459 A * 11/1999 Chiao et al. ................ 600/447
6,074,348 A * 6/2000 Chiao et al. ................ 600/443
6,132,377 A * 10/2000 Bolorforosh et al. ....... 600/458
6,213,951 B1 4/2001 Krishnan et al.

* cited by examiner

Primary Examiner—Ali M. Imam
(74) Attorney, Agent, or Firm—Oblon, Spivak, McClelland, Maier & Neustadt, P.C.

(57) ABSTRACT

Ultrasound diagnosis apparatus includes a transceiver unit, an adding processor, a filter, and an image processor. The transceiver unit insonifies an object injected with a contrast agent via an ultrasound transmission signal transmitted at a fundamental frequency f0 with at least two transmission rates. The adding processor adds a first component of the ultrasound echo signal and second component of the ultrasound echo signal. The first component is transmitted at a first rate of the at least two transmission rates and the second component is transmitted at a second rate of the at least two transmission rates. The filter suppresses at least a first frequency band of an addition result that is centered about a frequency 2·f0. The image processor then generates image data based on a suppressing result.

20 Claims, 10 Drawing Sheets